United States Patent
Hughes et al.

(10) Patent No.: US 7,610,813 B2
(45) Date of Patent: Nov. 3, 2009

(54) METHOD AND APPARATUS FOR A SELF-POWERED RFID-READABLE PEDOMETER

(75) Inventors: Robert D. Hughes, Tualatin, OR (US); Terry Dishongh, Portland, OR (US)

(73) Assignee: Intel Corporation, Santa Clara, CA (US)

( * ) Notice: Subject to any disclaimer, the term of this patent is extended or adjusted under 35 U.S.C. 154(b) by 13 days.

(21) Appl. No.: 11/529,548

(22) Filed: Sep. 29, 2006

(65) Prior Publication Data

US 2008/0082025 A1 Apr. 3, 2008

(51) Int. Cl.
*G01B 7/16* (2006.01)
(52) U.S. Cl. .......................... 73/777; 73/760
(58) Field of Classification Search ............ 73/760–777
See application file for complete search history.

(56) References Cited

U.S. PATENT DOCUMENTS

| | | | | |
|---|---|---|---|---|
| 5,142,805 A | * | 9/1992 | Horne et al. | 42/1.02 |
| 6,433,689 B1 | * | 8/2002 | Hovind et al. | 340/573.1 |
| 6,611,789 B1 | | 8/2003 | Darley | |
| 7,098,748 B2 | * | 8/2006 | Schmidt | 331/176 |
| 7,280,097 B2 | * | 10/2007 | Chen et al. | 345/156 |
| 7,328,131 B2 | * | 2/2008 | Donofrio et al. | 702/183 |
| 7,354,148 B2 | * | 4/2008 | Oishi | 347/104 |
| 7,355,519 B2 | * | 4/2008 | Grold et al. | 340/573.7 |
| 2005/0183292 A1 | | 8/2005 | DiBenedetto et al. | |
| 2006/0019135 A1 | * | 1/2006 | Curello et al. | 429/22 |
| 2006/0143645 A1 | | 6/2006 | Vock et al. | |
| 2006/0145660 A1 | * | 7/2006 | Black et al. | 320/108 |
| 2006/0174685 A1 | | 8/2006 | Skvortsov et al. | |

* cited by examiner

*Primary Examiner*—Max Noori
(74) *Attorney, Agent, or Firm*—Pillsbury Winthrop Shaw Pittman LLP

(57) ABSTRACT

A device, system and method for analyzing a user's motion using a piezoelectric film to generate a plurality of deformation signals based upon an associated plurality of deformations, an EEPROM to record data associated with the plurality of deformation signals, and a transceiver to receive at least a portion of the recorded data from the EEPROM and to transmit data, wherein the analysis may determine an abnormality in the user's gait.

21 Claims, 3 Drawing Sheets

METHOD AND APPARATUS FOR A SELF-POWERED RFID-READABLE PEDOMETER

FIELD OF THE INVENTION

The invention relates to self powered pedometers and a system and method of detecting gait abnormalities using the same.

BACKGROUND OF THE INVENTION

Pedometers, also referred to as step devices or step counters, are generally portable electronic devices which are worn by a person and are used to count each step the person makes. By counting the steps and performing simple calculations based on a user input stride length, pedometers are able to fairly accurately gauge the distance a person has walked or run. Pedometers generally use a pendulum which reacts to the users natural hip movement such that each step can be monitored. Pedometers generally have displays to allow users to monitor their progress.

DETAILED DESCRIPTION

Figure 1:
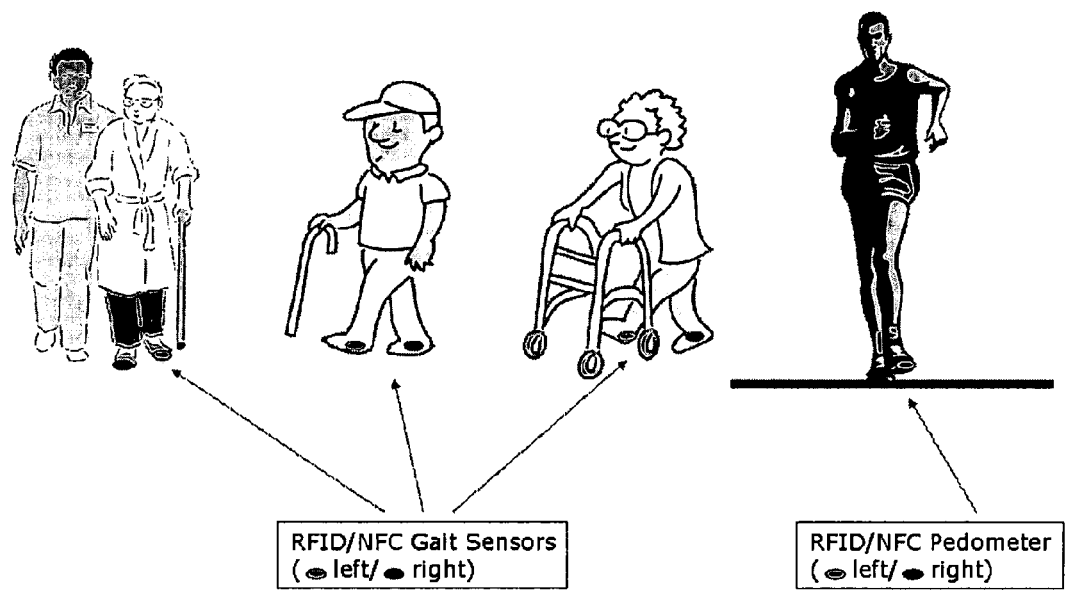
FIG. 1 depicts several exemplary uses for various devices and systems, according to various embodiments of the invention.

According to various embodiments of the invention, a device may comprise a piezoelectric film to generate a plurality of deformation signals based upon an associated plurality of deformations; an EEPROM to record data associated with the plurality of deformation signals; and an tranceiver to receive at least a portion of the recorded data from the EEPROM and to transmit data.

According to various embodiments of the invention, the EEPROM may further comprise an internal clock to generate timing data.

According to various embodiments of the invention, the RFID reader may receive the timing data from the internal clock.

According to various embodiments of the invention, the plurality of deformation signals may be used to determine a number of steps taken by an individual.

According to various embodiments of the invention, the piezoelectric film may be used to power the EEPROM.

According to various embodiments of the invention, the RFID tag may be a passive RFID tag.

According to various embodiments of the invention, a device may further comprise an accelerometer to generate acceleration data to be transmitted to the EEPROM.

According to various embodiments of the invention, the piezoelectric film may be used to power the accelerometer.

According to various embodiments of the invention, the device may be removably attached to a shoe.

According to various embodiments of the invention, the piezoelectric film may be configured to be deformed by a heel and a toe of a user wearing the shoe.

According to various embodiments of the invention, the transceiver may be an RFID tag.

According to various embodiments of the invention, the transceiver may be an NFC device.

According to various embodiments of the invention, an apparatus may comprise a device, wherein the apparatus is a footwear or a piece of clothing.

According to various embodiments of the invention, a device may comprise a piezoelectric film to generate a deformation signal, and an RFID tag to receive data from the piezoelectric film and to transmit the data to an external device, wherein the device is a pedometer.

According to various embodiments of the invention, a device may further comprise an accelerometer.

According to various embodiments of the invention, the piezoelectric film may be used to power the accelerometer.

According to various embodiments of the invention, the device may be removably attached to a shoe.

According to various embodiments of the invention, a device may comprise a piezoelectric film to generate a plurality of deformation signals based upon an associated plurality of deformations, a real time clock to generate timing data, an EEPROM to record data associated with the plurality of compression signals and the timing data, and an tranceiver to receive at least a portion of the recorded data from the EEPROM and to transmit at least a portion of the received data.

According to various embodiments of the invention, the transceiver may be an RFID tag.

According to various embodiments of the invention, the transceiver may be an NFC device.

According to various embodiments of the invention, an apparatus may comprise the device and the apparatus may be a footwear or a piece of clothing.

According to various embodiments of the invention, a device may further comprise a processor to analyze the deformation signals to determine abnormalities in a user's step.

According to various embodiments of the invention, the deformation signals may be analyzed in relation to the timing data.

According to various embodiments of the invention, a system for diagnosing a user's gait may comprise a plurality of the devices according various other embodiments of the invention, the plurality of the devices comprising a first device and a second device, a reader to receive data from the transceivers of the first and second devices, and a processor to receive the data from the reader, wherein the processor is configured to analyze the deformation signals generated by the first and second devices.

According to various embodiments of the invention, the first device and the second device may be removably attached to a footwear.

According to various embodiments of the invention, the processor may be configured to analyze the deformation signals generated by the plurality of the devices to determine if there is an abnormality in a user's gait.

According to various embodiments of the invention, a duration of the deformation signals may be analyzed According to various embodiments of the invention, an amplitude of the deformation signals may be analyzed.

According to various embodiments of the invention, an amplitude of the deformation signals may be analyzed with respect to the duration of the deformation signals.

According to various embodiments of the invention, the reader may be an RFID reader.

According to various embodiments of the invention, a deformation signal generated by the first device and a deformation signal generated by the second device may be compared to diagnose the user's gait.

According to various embodiments of the invention, a method of diagnosing a user's gait may comprise obtaining or manufacturing a system according to various other embodiments of the invention, transmitting data from the first and second devices to a processor, and analyzing the deformation signals generated by the first and second devices.

According to various embodiments of the invention, a method may further comprise producing data related to a user's gait based on the analyzing of the deformation signals.

According to various embodiments of the invention, the analyzing the deformation signals may comprise analyzing a duration of the deformation signals.

According to various embodiments of the invention, the analyzing the deformation signals may comprise analyzing an amplitude of the deformation signals.

As used in the specification and claims, the singular forms "a", "an" and "the" include plural references unless the context clearly dictates otherwise.

RFID technology is commonly utilized for identifying objects. The heart of an RFID system lies in an information carrying tag called an RFID tag, which functions in response to a coded RF signal received from a base station or an RFID reader. Typically, an RFID tag reflects an incident RF carrier back to the base station or reader, and information is transferred as the reflected signal is modulated by the RFID tag according to its programmed information protocol.

Generally an RFID tag has a semiconductor chip having RF circuits, various logic circuitry, and a memory, as well as an antenna, a collection of discrete components, such as capacitors and diodes, a substrate for mounting the components, interconnections between components, and a physical enclosure. Two types of RFID tags are generally used, active tags, which utilize batteries, and passive tags, which are either inductively powered or powered by RF signals used to interrogate the tags; passive tags do not use a battery.

Generally, passive RF tags contain of two basic parts: an analog circuit which detects and decodes the RF signal and provides power to a digital portion of the tag using RF field strength from the reader, and a digital circuit which implements multiple items of tag identification protocol.

A radio frequency (RF) identification system generally consists of an RF reader and a plurality of RF tags. In a typical configuration, the reader utilizes a processor which issues commands to an RF transmitter and receives commands from the RF receiver. The commands serve to identify tags present in the RF field.

In some implementations, commands exist to gather information from the tags. In more advanced systems, commands exist which output information to the tags. This output information may be held temporarily on the tag, it may remain until written over, or it may remain permanently on the tag.

The RF transmitter of the reader generally encodes commands from the processor, modulates the commands from a base band to the radio frequency, amplifies the commands, and then passes the commands to the RF antenna. The RF receiver receives the signal at an antenna, demodulates the signal from the RF frequency to the base band, decodes the signal, and passes it back to the processor for processing. The reader's antenna is usually capable of transferring RF signals to and from a plurality of tags within the RF signal range.

Radio Frequency Identification is a type of automatic identification method, which utilizes storing and remotely retrieving data using devices called RFID tags or transponders. Chip-based RFID tags generally contain silicon chips and antennas. Passive tags generally do not use an internal power source, whereas active tags generally do incorporate a power source. RFID cards, also known as "proximity" or "proxy" cards, come in three general varieties: passive, semi-passive (also known as semi-active) and active.

Passive RFID tags generally have no internal power supply. A minute electrical current induced in an antenna by incoming radio frequency signals generally provide enough power for an integrated circuit (hereinafter, "IC"), e.g. a CMOS based IC, in the tag to power up and transmit a response. Most passive tags provide a signal by backscattering the carrier signal received from an RFID reader. In order to utilize backscattering, the antenna of a passive RFID tag is generally configured to collect power from the incoming signal and to transmit an outbound backscatter signal. The response of a passive RFID tag is not limited to an ID number (e.g. GUID); many RFID tags contain nonvolatile memory devices, such as EEPROMs, for storing data.

Because passive RFID tags do not generally utilize an onboard power supply, and because they do not require any moving parts, these RFID tags can be very small, and may have a nearly unlimited life span. Commercially available products exist that may be embedded under the skin of a person or animal. For example, RFID tags are commonly smaller than 0.15 mm×0.15 mm×7.5 µm. RFID tags, such as those used by many major retail chains, are often available at a minimal cost. The addition of large antennas for specific applications may result in RFID tags the size of a post card, or perhaps even larger. Common passive RFID tags may commonly be read at distances ranging from about 10 cm to a several meters, depending on the chosen radio frequency and antenna design/size. Due to the simplicity of the design of passive RFID tags, the tags may be suitable for manufacture using a printing process for the antennas.

Non-silicon tags made from polymer semiconductors, having operating frequencies greater than 13.56 MHz, may be used. These polymer tags may be roll printable, like a magazine, and accordingly may be much less expensive than silicon-based tags.

Unlike passive RFID tags, active RFID tags generally have internal power sources which are used to power incorporated ICs that generate an outgoing signal. Active tags may be more reliable (e.g. fewer errors) than passive tags because the active tags may conduct a session with a reader where error correction and/or signal verification may be utilized. Active tags may also transmit at higher power levels than passive tags, allowing them to be more effective in "RF challenged" environments such as water or metal, and over greater distances. Many active RFID tags have practical ranges of hundreds of meters, and a battery life of up to 10 years.

RFID tags may be used with humidity, shock/vibration, light, radiation, temperature, atmospheric and/or other sensors. Active tags typically have longer range (approximately 300 feet) and larger memories than passive tags, as well as the ability to store additional information sent by the transceiver.

In a typical RFID system, an RFID reader may be contain an antenna packaged with a transceiver and decoder. The RFID reader may emit a signal activating the RFID tag so it can read data from and write data to the RFID tag. When an RFID tag passes through the electromagnetic zone, it detects the reader's activation signal and is activated. The reader may then decode the data encoded in the tag's IC and may either store the data of pass the data to a processor.

Depending on the type of system utilizing the RFID reader, application software on a host computer may process the data in a myriad of different ways, e.g. the data may be filtered to reduce redundant readings of the same tag and to form a smaller and more useful data set.

RFID tags may be used to replace UPC or EAN barcodes. Generally, RFID tags have a high data capacity that may be used to store a unique code that may be used to individually track shipped items, in contrast to bar codes which are limited to a single type code for all instances of a particular product. This may help companies to combat theft and other forms of product loss. Moreover, the tracing back of products is an important feature that gets well supported with RFID tags containing not just a unique identity of the tag but also the serial number of the object. This may help companies cope with quality deficiencies and resulting recall campaigns-and it also assists in post-sale tracking and profiling of consumers.

A concern surrounding RFID technology is the illicit tracking of RFID tags. Tags which are world-readable pose a risk to both personal location privacy and corporate/military security. More generally, privacy organizations have expressed concerns in the context of ongoing efforts to embed electronic product code (EPC) RFID tags in consumer products.

Some RFID systems may utilize cryptography to prevent tag cloning. Some RFID tags may use a "rolling code" scheme, wherein the tag identifier information changes after each scan, thus reducing the usefulness of observed responses. More sophisticated devices may engage in challenge-response protocols where the tag interacts with the reader. In these protocols, secret tag information is never sent over the insecure communication channel between tag and reader. Rather, the reader issues a challenge to the tag, which responds with a result computed using a cryptographic circuit keyed with some secret value. Such protocols may be based on symmetric or public key cryptography. Cryptographically-enabled tags may have higher cost and power requirements compared to other tags.

An alternate embodiment of the invention relates to determining the orientation of packages in a warehouse. Currently, warehouses are able to tell the location of a package by attaching Radio Frequency Identification (hereinafter, "RFID") tags to the packages. To determine the orientation of the packages, warehouse employees must physically inspect the packages.

Manufacturers, distributors and/or retailers have a need to track their products, and they conventionally attach RFID tags to each product to identify and track their merchandise. By the transmission and reception of radio signals to and from the RFID tags on the products, the products can be tracked from the time of manufacture to the time of sale without any direct visual or physical contact with the product being monitored. Various information may be stored in an RFID tag; for RFID tags attached to products, this information typically includes a retail SKU number (e.g., UPC—universal product code) identifying the name, manufacturer and/or suggested price of the product, a unique serial number identifying the product, or a combination of the SKU number and the unique serial number. Merchants also use SKU numbers to keep track of inventory so that they know which products are selling well and when to reorder products from wholesalers. The unique serial number stored in a RFID tag can be a globally unique number or a number assigned in series to products manufactured in the same product category.

A typical RFID tag on a product includes an antenna and a silicon chip containing modulation circuits, control logic and non-volatile memory. The silicon chip derives electrical power from radio signals received by the antenna or from a battery, and is able to exchange data with a RFID tag scanner by demodulating and modulating the radio signals.

While some users prefer to use a display to constantly monitor their progress, other users prefer to wear their pedometers throughout the course of a day and are more interested in their cumulative progress.

According to various aspects of the invention, an Electrically Erasable Programmable Read-Only Memory (hereinafter, "EEPROM") may be a non-volatile storage chip used in computers and other devices to store data. EEPROM chips may use serial interfaces to connect to other devices.

EEPROMs typically come in a range of capacities from a few bytes to over 128 kilobytes and are often used to store configuration parameters. In some systems, EEPROMs have been used in lieu of CMOS nonvolatile BIOS memory. For example, in personal computers EEPROMs are often used to store the BIOS code and related system settings. EEPROMs may be erased electrically in-circuit, and may be used for 100,000 erase-write cycles or more. EEPROMs typically retain data when power is not supplied.

Typically, a transceiver is a device that has a transmitter and a receiver which may be combined. Technically, transceivers generally combine a significant amount of the transmitter and receiver handling circuitry. Similar devices may include transponders, transverters, and repeaters. Generally, a transceiver combines both transmission and reception capabilities within a single housing. The term transceiver, as used herein may refer to a device, such as an RFID tag or an NFC device. These devices may receive data over a hardwired connection or a radio frequency connection, as well as through various other types of connection. The devices may transmit information over similar of different connections.

An accelerometer is a device for measuring acceleration. Accelerometers generally measure their own motion, in contrast to devices based on remote sensing. One type of accelerometer, is formed as a micro electromechanical system (hereinafter, "MEMS") device; and often comprises little more than a suspended cantilever beam or proof mass (also known as seismic mass) with some type of deflection sensing and circuitry. MEMS Accelerometers are available in a wide variety of ranges up to thousands of orders in magnitude of gravity, and are available in multiple axis designs. The devices have been used throughout development and practice of understanding human kinematic motion and gait. Knowing the acceleration of the component of the human body, one can easily perform a temporal integration to arrive at the velocity or even the know displacement of a body segment. When the accelerometers are placed in the shoe of a person the data gathered from the device enables the understanding of gait, steps taken and abnormality which may arise in the walking or stance of an individual.

Increasingly, low-cost accelerometers have been integrated into commercial, industrial and consumer products on an OEM level, making many cost-sensitive monitoring applications economically viable. These low-cost MEMS sensors have generally utilized a micro-machined silicon structure. With recent advances in ceramic processing and production, the term MEMS is now broadening beyond silicon to include a new generation of low-cost piezoelectric sensors which rival silicon-based MEMS in price and offer distinct performance advantages for many applications.

Because piezoelectric sensors often require less complicated circuitry than silicon-based MEMS devices, it is possible to achieve lower noise for a given cost. Low-impedance PE sensors generally have lower noise floors than either VC or PR designs. Recent advances in low power solid-state electronics have enabled the manufacture of provide high performance sensors with remarkably low power consumption. PE sensors have also been designed to measure frequencies as low as 0.1 Hz, and as high as 10 kHzs. Furthermore, due to the nature of their design, PE sensors can be configured as monolithic blocks capable of withstanding extreme shock levels.

Accelerometers convert motion into measurable electrical signals. Three primary technologies are employed in low-cost accelerometer designs: piezoelectric (PE), piezoresistive (PR) and variable capacitance (VC). Piezoelectric sensors generally use piezoelectric crystals (natural or ceramic) which generate a charge proportional to induced stress. PR and VC accelerometers generally use micro-machined silicon structures to create either a change in resistance or a change in capacitance proportional to acceleration.

Piezoelectric materials generate an electrical charge proportional to stress incurred on the material. Piezoelectric thin films are commonly used in transducers to measure force loads and pressures. This charge can be measured directly as a high-impedance signal (charge mode), or converted into a low-impedance voltage output by internal electronics. Integrated electronics may be used to condition an output signal, thereby allowing for the use of relatively simple electronic circuitry. Typically, this electronic circuitry is a variant of a Wheatstone bridge of resistors or a simple analog to digital gain converter.

Simple electrical theory shows that the resistance of any conductive materials is a function of cross section of the material and the length of a signal. Using this physical property, strain gage sensors may be used in combination with a Wheatstone bridge in which one or more legs change value when strained as the bridge becomes un-balanced. These sensors utilize applied current and signal-conditioning electronics.

Variable capacitance sensors may be regarded as parallel plate air gap capacitors. As acceleration acts on the silicon structure, the gap varies, thereby changing the capacitance. The changing capacitance is converted into a measurable signal using current detectors. The electronics utilized for the conversion are quite complex and generally include a high-frequency oscillator.

Near Field Communication (hereinafter, "NFC") is a new, short-range wireless connectivity technology that evolved from a combination of existing contact free identification and interconnection technologies. Products with built-in NFC may simplify the way consumer devices interact with one another, helping speed connections, receive and share information and even making fast and secure payments.

Commonly operating at 13.56 MHz and transferring data at up to 424 Kbits/second, NFC provides intuitive, simple, and safe communication between electronic devices. NFC is both a "read" and "write" technology. Communication between two NFC-compatible devices may occur when the devices are brought within approximately four centimeters of one another: a simple wave or touch may establish an NFC connection which is then compatible with other known wireless technologies such as Bluetooth or Wi-Fi. Because the transmission range may be relatively short, NFC-enabled transactions are inherently secure. Also, physical proximity of the device to the reader gives users the reassurance of being in control of the process.

NFC may be used with a variety of devices, from mobile phones that enable payment or transfer information to digital cameras that send their photos to a TV set with just a touch.

According to various embodiments of the invention, a device may comprise a piezoelectric film to generate a plurality of deformation signals based upon an associated plurality of deformations, an EEPROM to record data associated with the plurality of deformation signals, and an RFID tag to receive at least a portion of the recorded data from the EEPROM and to transmit data.

According to these embodiments of the invention, a piezoelectric film may be removable or fixedly attached to a shoe. For example, the film may be placed in the shoe or it may be integrated into the shoe. In some embodiments of the invention, the piezoelectric film may be large enough to be deformed by both heel and toe strikes of a user. In other embodiments, the film may be sized to record only toe or heel strikes. In yet further embodiments, a plurality of films may be used to record strikes from different areas of a user's foot.

According to these embodiments, when a user is wearing a shoe having a piezoelectric film, when the user takes a step the film is deformed in some way. For example, the deformation may be a compression of the film of a bending of the film. When the film is deformed, a voltage is generated in proportion to the deformation. This voltage may be used to form a deformation signal which may be transmitted to an EEPROM which is able to store information related to the signal. In some of the embodiments, the stored information may simply be a counter that increments every time a certain threshold voltage is exceeded, in other embodiments, the information may include more detailed information such as the exact form of the deformation signal as well as a timing related to the deformation.

While a system in which a device is attached to a shoe is described, the invention is not limited to such a system. Devices according to various embodiments of the invention may be used in a variety of ways. For example, the devices may be incorporated into shoes or other footwear, the devices may be used in clothing, such as socks, or the devices could be attached directly to a user, along with various other configurations.

According to various embodiments of the invention, the EEPROM may be powered by the piezoelectric film such that the deformation signals are not only recorded, but the associated generated voltage is used to power the EEPROM. These embodiments may also comprise an RFID tag with a unique identification number associated with it. As the information on the tag is collected from the system, the data may be stored in EEPROMs or flash memory. Hence, if the device comes within proximity of an external RFID reader, the embedded RFID tag is activated and the information contained in the memory is read. This information may be transmitted to the RFID reader through common known radio protocols. According to various embodiments of the invention, the RFID tag is a passive tag that may be charged by an external magnetic field or by the voltage generated by the piezoelectric film.

In a simple embodiment, the device may be a pedometer that merely records a number of steps taken by a user based on the deformation signals. According to some embodiments, a threshold voltage may be set such that the device is able to discriminate between actual steps taken and simple shuffling of the feet. For example, if a user desired a very accurate step count during a run, the threshold level may be set at a higher level that would only be exceeded by deformations associated with running rather than smaller deformations that may be associated with jogging in place. As depicted in FIG. 1, a second device may be worn in a user's second shoe.

By using two devices, more information can be generated. This information may be used by a variety of people, for example runners or other athletes may use these devices to help maximize their performance, casual walkers curious as to how far they have traveled may use the devices to track their progress, or elderly or injured users may use the devices to help diagnose or predict irregularities in their steps. Data gathered using these devices can be analyzed to determine walking ability, standing ability, walking symmetry, health of walk or gait, the onset of mobility deterioration due to various factors and also as a pedometer for fitness applications. The data can also be used to determine over-reliance of one leg relative over the other and may provide early detection of various physical ailments related to the back, hips and lower body.

Figure 2:
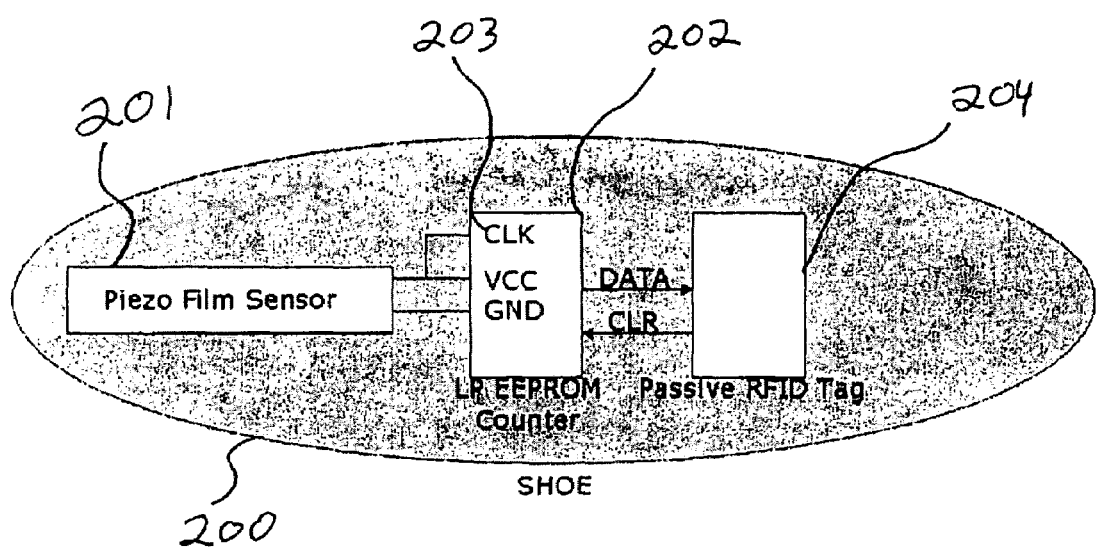
FIG. 2 depicts an exemplary self powered pedometer device, according to various embodiments of the invention.

As shown in FIG. 2, a device 200 according to various embodiments of the invention, may utilize a piezo film sensor 201 to generate deformation signals when it is deformed. A low power EEPROM 202, which may be powered by the piezo film sensor 201, may be used to record information related to the deformation signals. In some embodiments, the EEPROM 202 may utilize a clock 203 to generate timing data which may be used to supplement the deformation data. The device may also use an RFID tag 204, which may be a passive RFID tag, to transmit the information to an external reader. The RFID tag 204 may also transmit a clear signal CLR to the EEPROM 202 to indicate that the data should be cleared from the EEPROM 202. The signal may be sent whenever the currently stored data is transmitted to an external processor where it may be examined.

In a more complex embodiment, for example one in which toe strikes and heel strikes are used to generate deformation signals, the device may be used to help diagnose a user's gait or stride to help determine if the user has abnormalities that may lead to more sever conditions. For example, the time between a toe strike and a heel strike might be used, this information may be compared against similar information from a user's other shoe to determine an inconsistency in the user's gait. Furthermore, the strength of the deformation signal may be monitored over time to determine if a user's foot starts to land at a different angle, or if the user is favoring one foot over the other. A change in the strength of the signal may indicate that the film is being deformed differently, or if the film is being compressed from a different angle. Accordingly, any changes or differences in the compression signals may be used to help diagnose a user.

According to various embodiments of the invention, a diagnostic device may comprise a piezoelectric film to generate a plurality of deformation signals based upon an associated plurality of deformations, a real time clock to generate timing data, an EEPROM to record data associated with the plurality of compression signals and the timing data; and an RFID tag to receive at least a portion of the recorded data from the EEPROM and to transmit at least a portion of the received data.

Figure 3:
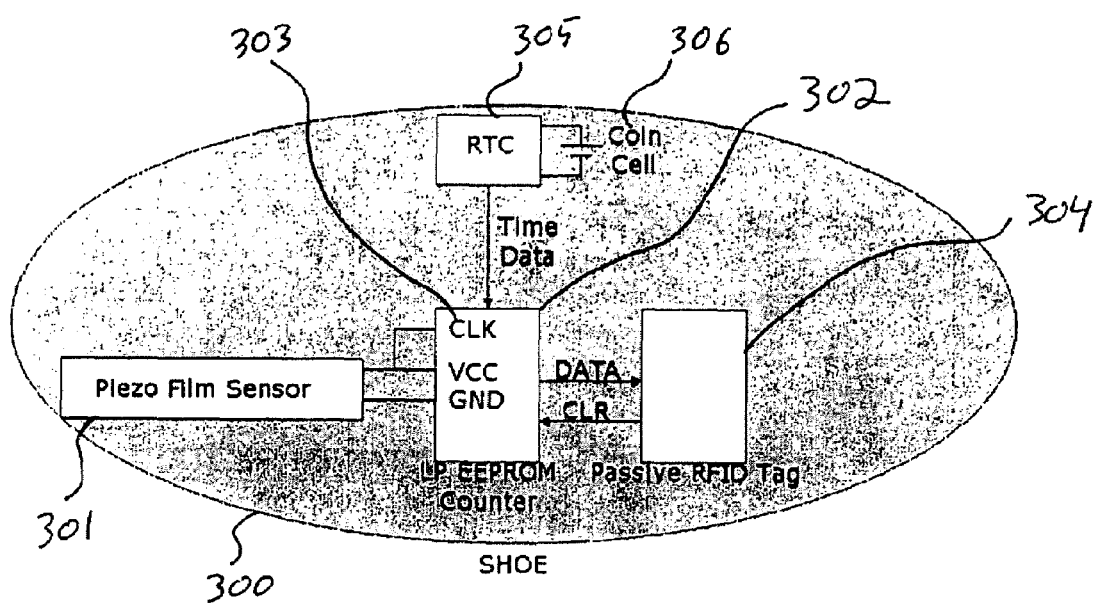
FIG. 3 depicts an exemplary self powered diagnostic device, according to various embodiments of the invention.

According to various embodiments of the invention, a device may also include a clock, such as a real time clock, to provide timing data which may be used in association with the deformation signals to provide more detailed information to a user or to assist in diagnosing the user. The human gait, either walking or running, may be subjected to 4-12 Hz signal variations. In order to gain information about a gait which may aide in a diagnostic understanding, it may be helpful to determine accelerations which vary in the tenths of second. Typically, silicon devices which are externally or internally clocked for performance do not have the consistency to precisely differentiate signals to this degree over an extended course of time, for example, over a half hour. However, a real time clock which has minimal temporal drift may be added to the system increase performance and base knowledge of gait pattern differentiations. As shown in FIG. 3, which depicts a device 300 having a piezo film sensor 301, an EEPROM 302, having an integrated clock 303, and an RFID tag 304, a real time clock 305 may be used to generate additional timing data which may be used to help diagnose a user's gait. The real time clock 305 may be powered by a coin cell 306 as shown. According to other embodiments, the real time clock 305 may be powered by the piezo film 301.

According to various embodiments of the invention, data may be transferred from the devices into an external processor, where the data can be analyzed using a software. application and based upon the step time and relative time delta between steps, gait can be calculated. In some embodiments, the real time clocks are not synchronized because only relative time differences between steps are used for gait calculation and analysis. For example, for the case of an elderly walker, the system could analyze the relationship between the left and right feet and the symmetry of the walk to determine walk health and distance walked. Additionally, it could optionally incorporate an accelerometer for more complex analysis or the counter could be replaced with an analog to digital converter to analyze irregularities in walking. For pedometer applications, the analysis could range from simple conversion of steps run to a distance or may optionally incorporate more complex analysis such as running symmetry.

According to various embodiments of the invention, a system for diagnosing a user's gait may comprise a first diagnostic device to be attached into a first shoe, a second diagnostic device to be attached to a second shoe, an RFID reader to receive data from the RFID transmitters of the first and second diagnostic devices, and a processor to receive the data from the RFID reader, wherein the processor is configured to analyze the deformation signals generated by the first and second diagnostic devices.

According to various embodiments of the invention, a method of diagnosing a user's gait may comprise attaching a first diagnostic device to a first shoe, attaching a second diagnostic device to a second shoe, wherein the diagnostic devices comprise, a piezoelectric film to generate a plurality of deformation signals based upon an associated plurality of deformations, a real time clock to generate real time data, an EEPROM to record data associated with the plurality of deformation signals and the timing data, and an RFID tag to receive at least a portion of the recorded data from the EEPROM and to transmit at least a portion of the received data, transmitting data from the first and second diagnostic devices to a processor, and analyzing the deformation signals generated by the first and second diagnostic devices.

According to various embodiments of the invention, a self powered pedometer device to be removably attached to a shoe may comprise a piezoelectric film to generate a plurality of deformation signals based upon an associated plurality of deformations, an EEPROM comprising an internal clock to generate timing data, wherein the EEPORM is configured to record data associated with the plurality of deformation signals and the timing data, and an NFC device to receive at least a portion of the recorded data from the EEPROM and to transmit at least a portion of the received data.

According to various embodiments of the invention, a method of diagnosing a user's gait may comprise attaching a first diagnostic device to a first shoe, attaching a second diagnostic device to a second shoe, wherein the diagnostic devices comprise, a piezoelectric film to generate a plurality of deformation signals based upon an associated plurality of compressions, a real time clock to generate real time data, an EEPROM to record data associated with the plurality of deformation signals and the timing data, and an NFC device to receive at least a portion of the recorded data from the EEPROM and to transmit at least a portion of the received data, transmitting data from the first and second diagnostic devices to a processor, and analyzing the deformation signals generated by the first and second diagnostic devices.

Because various embodiments of the invention are self powered by a piezoelectric film, these embodiments do not require the use of batteries and may therefore require less maintenance and may be environmentally friendly.

According to various embodiments of the invention, a device may have a thickness of 5 mils as a result of using only silicon passives. A thickness of a device may be determined by the stack height of the silicon used in constructing the device along with the commonly available passives and the substrates they are adhered to. These devices may be easily incorporated into footwear.

The invention claimed is:

1. A device, comprising:
   a piezoelectric film to generate a plurality of deformation signals based upon an associated plurality of deformations;
   a real time clock to generate timing data;
   an EEPROM to record data associated with the plurality of compression signals and the timing data;
   an RFID tag to receive at least a portion of the recorded data from the EEPROM and to transmit at least a portion of the received data; and
   a processor to analyze the deformation signals to determine abnormalities in a user's step,
   wherein the device is a pedometer or gait sensor.

2. An apparatus comprising the device of claim 1, wherein the apparatus is a footwear or a piece of clothing.

3. The device of claim 1, wherein the deformation signals are analyzed in relation to the timing data.

4. A system for diagnosing a user's gait, the system comprising:
   a plurality of the devices according to claim 1, the plurality of the devices comprising a first device and a second device;
   a reader to receive data from the transceivers of the first and second devices; and a processor to receive the data from the reader;
   wherein the processor is configured to analyze the deformation signals generated by the first and second devices.

5. The system of claim 4, wherein the first device and the second device are removably attached to a footwear.

6. The system of claim 4, wherein the processor is configured to analyze the deformation signals generated by the plurality of the devices to determine if there is an abnormality in a user's gait.

7. The system of claim 4, wherein a duration of the deformation signals is analyzed.

8. The system of claim 4, wherein an amplitude of the deformation signals is analyzed.

9. The system of claim 4, wherein an amplitude of the deformation signals is analyzed with respect to the duration of the deformation signals.

10. The system of claim 4, wherein the reader is an RFID reader.

11. The system of claim 4, wherein a deformation signal generated by the first device and a deformation signal generated by the second device are compare to diagnose the user's gait.

12. A method of diagnosing a user's gait, the method comprising:
    obtaining or manufacturing a system for diagnosing a user's gait, the system comprising:
    a plurality of the devices, each device comprising a piezoelectric film to generate a plurality of deformation signals based upon an associated plurality of deformations; a real time clock to generate timing data; an EEPROM to record data associated with the plurality of compression signals and the timing data; and an a transceiver to receive at least a portion of the recorded data from the EEPROM and to transmit at least a portion of the received data, the plurality of the devices comprising a first device and a second device; a reader to receive data from the transceivers of the first and second devices; and a processor to receive the data from the reader; wherein the processor is configured to analyze the deformation signals generated by the first and second devices;
    transmitting data from the first and second devices to a processor; and
    analyzing the deformation signals generated by the first and second devices.

13. The method of claim 12, further comprising producing data related to a user's gait based on the analyzing of the deformation signals.

14. The system of claim 12, wherein the analyzing the deformation signals comprises analyzing a duration of the deformation signals.

15. The system of claim 12, wherein the analyzing the deformation signals. comprises analyzing an amplitude of the deformation signals.

16. A system for diagnosing a user's gait, comprising:
    a plurality of the devices, each device comprising a piezoelectric film to generate a plurality of deformation signals based upon an associated plurality of deformations; a real time clock to generate timing data; an EEPROM to record data associated with the plurality of compression signals and the timing data; and an a transceiver to receive at least a portion of the recorded data from the EEPROM and to transmit at least a portion of the received data, the plurality of the devices comprising a first device and a second device; a reader to receive data from the transceivers of the first and second devices; and a processor to receive the data from the reader; wherein the processor is configured to analyze the deformation signals generated by the first and second devices;
    wherein the first and second devices are configured to transmit data to a processor that is configured to analyze the deformation signals generated by the first and second devices.

17. The device of claim 1, wherein the device contains no batteries and electrical power in the device is self generated.

18. The device of claim 1, wherein the device contains no batteries and electrical power in the device is self generated.

19. The device of claim 17, wherein the device is a pedometer or a gait sensor.

20. The device of claim 18, wherein the device is a pedometer or gait sensor.

21. The method of claim 12, further comprising measuring a time between a heel strike and a toe strike.

* * * * *